United States Patent [19]

Shinohara

[11] 4,258,132

[45] Mar. 24, 1981

[54] PROCESS FOR PRODUCING AN AGGLUTINATING SUBSTANCE UTILIZING DEMATIUM ATCC 20524

[76] Inventor: Satoru Shinohara, No. 8-14, Takasago-cho, Hyuga-shi, Miyazaki-ken, Japan

[21] Appl. No.: 948,227

[22] Filed: Oct. 3, 1978

[30] Foreign Application Priority Data

| Oct. 11, 1977 | [JP] | Japan | 52-121687 |
| Aug. 10, 1978 | [JP] | Japan | 53-97664 |
| Aug. 17, 1978 | [JP] | Japan | 53-100150 |

[51] Int. Cl.$^3$ .................... C12P 19/04; C12R 1/645
[52] U.S. Cl. .................... 435/101; 435/171; 435/911
[58] Field of Search ............... 435/101, 171, 911, 102; 536/1

[56] References Cited

U.S. PATENT DOCUMENTS

| 3,320,136 | 5/1967 | Zajic | 435/102 |
| 3,406,114 | 10/1968 | Goren | 435/101 |
| 4,004,977 | 1/1977 | Kato et al. | 435/102 |

OTHER PUBLICATIONS

Kato, et al., "Pullulan", *Chem. Abstracts*, vol. 81, No. 8, p. 119 (1974), Abs. No. 39359w.
Kato, et al., "Pullulan", *Chem. Abstracts*, vol. 79, No. 3, p. 318 (1973), Abs. No. 16917w.
Komoto, et al., "Oligosaccharides and Polysaccharides Produced by *Dematium Pullulans* from Sucrose", *Chem. Abstracts*, vol. 70, No. 19, p. 86 (1969), Abs. No. 85128v.

*Primary Examiner*—Thomas G. Wiseman
*Attorney, Agent, or Firm*—Armstrong, Nikaido, Marmelstein & Kubovcik

[57] ABSTRACT

The present invention relates to a process for producing an agglutinating substance having an agglutination activity for not only proteins but also organic substances, inorganic substances, minerals and living germs by culturing an agglutinating substance-producing microorganism belonging to Dematium (Dematiaceae) and a process for agglutinating and sedimenting inorganic and organic, insoluble suspensoids, colloid substances, insoluble proteins or soluble proteins contained in water or various industrial wastes by using the agglutinating substances.

3 Claims, 26 Drawing Figures

FIG. I
(a)
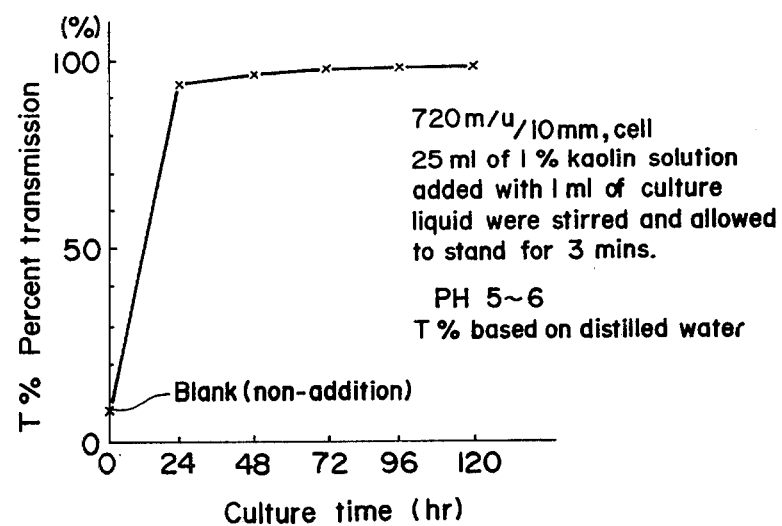
(b)
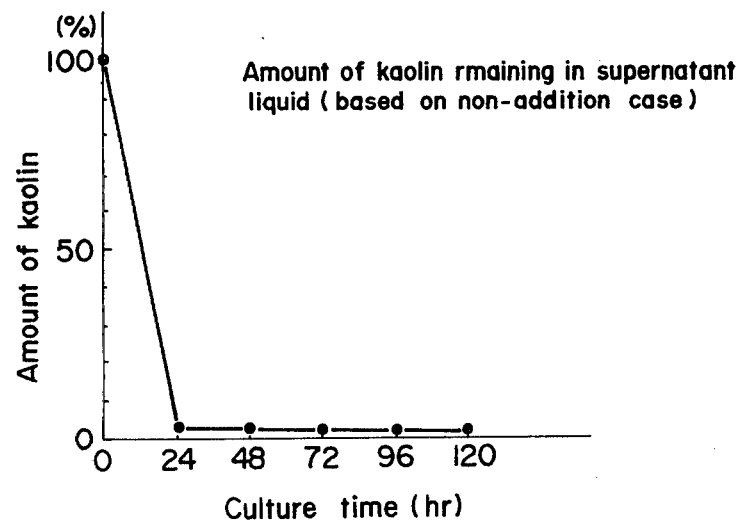

(a)

(b)

FIG. 7
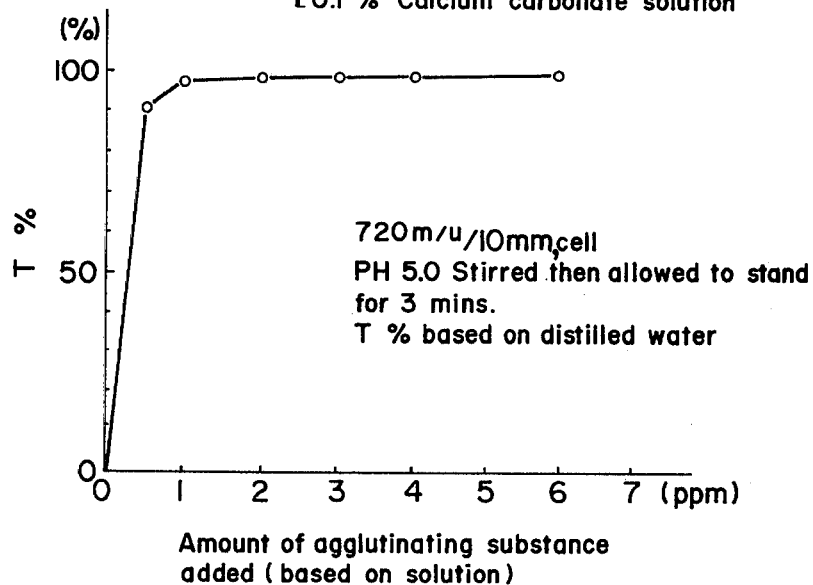
(a)
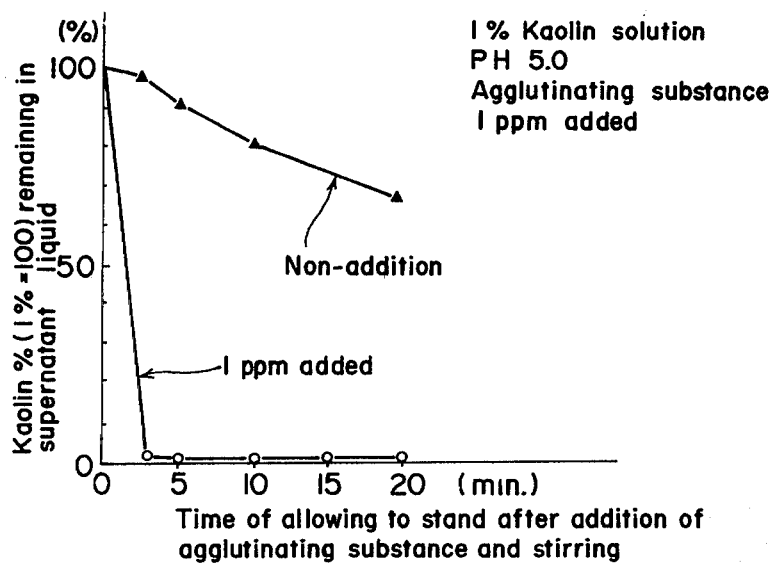
(b)

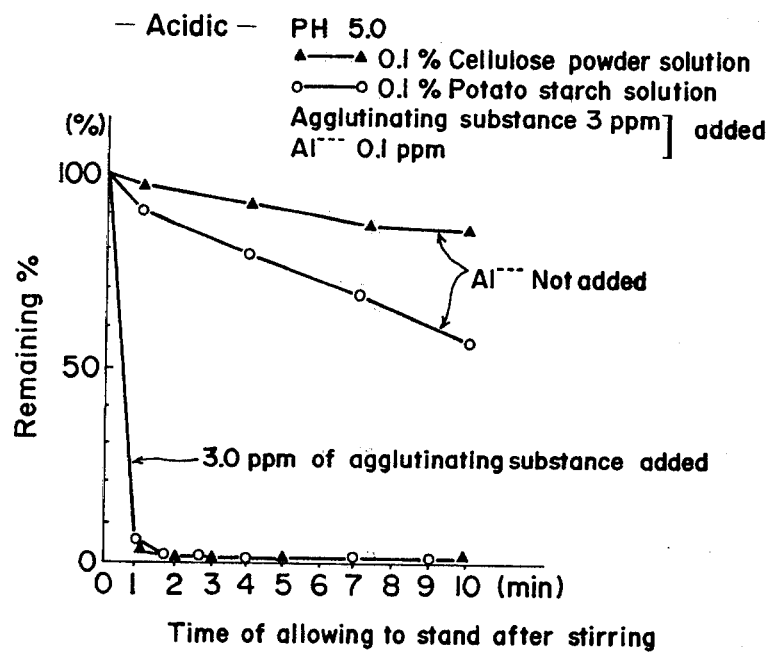
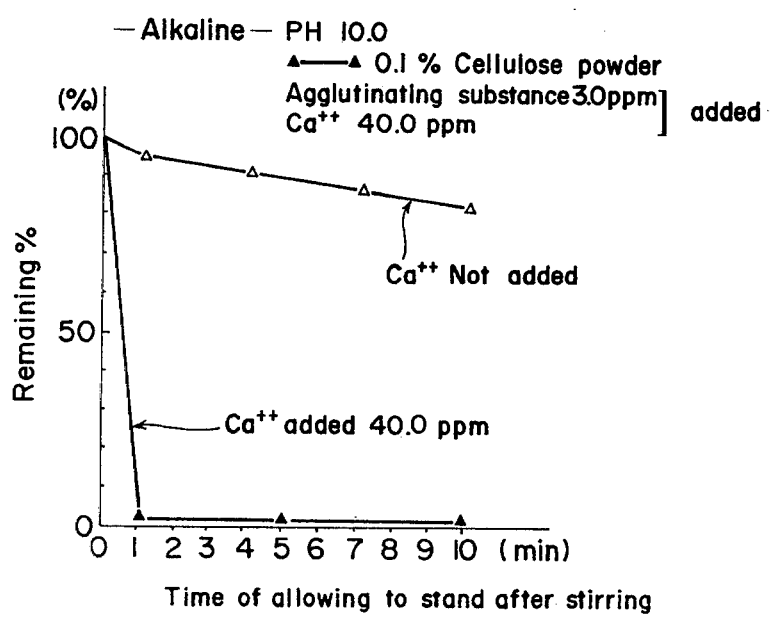

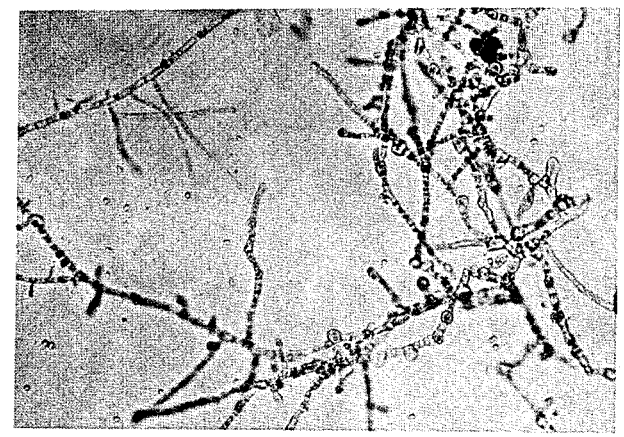
FIG. 12 ×150
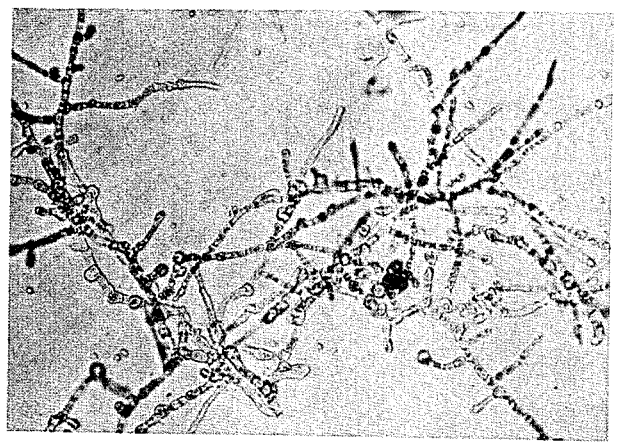
FIG. 11 ×150
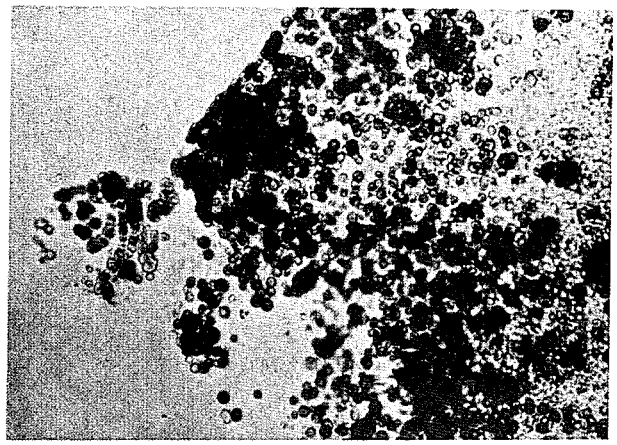
FIG. 10 ×60

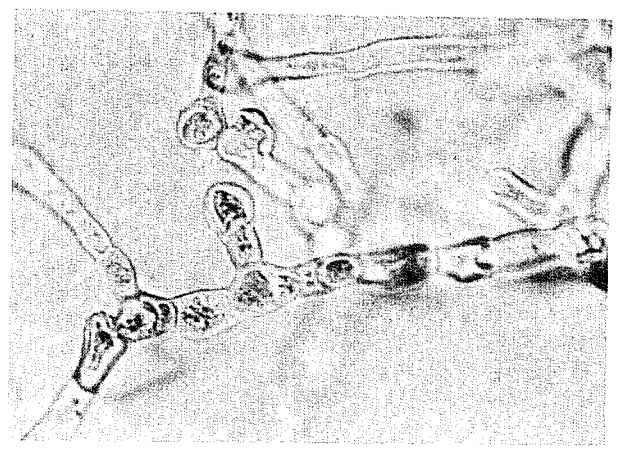
FIG. 15 ×600
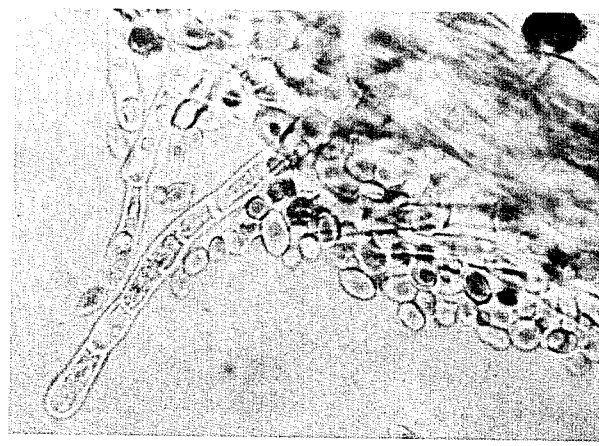
FIG. 14 ×600
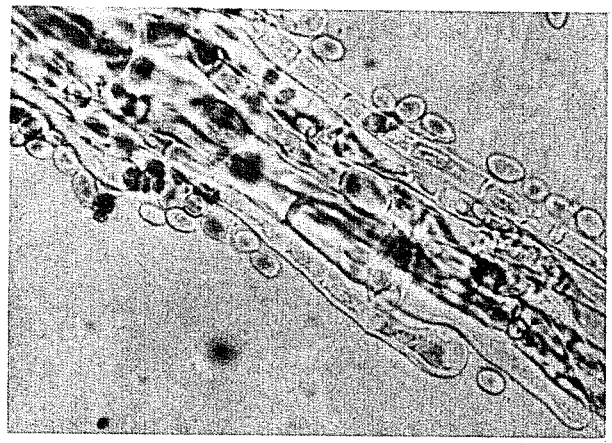
FIG. 13 ×600

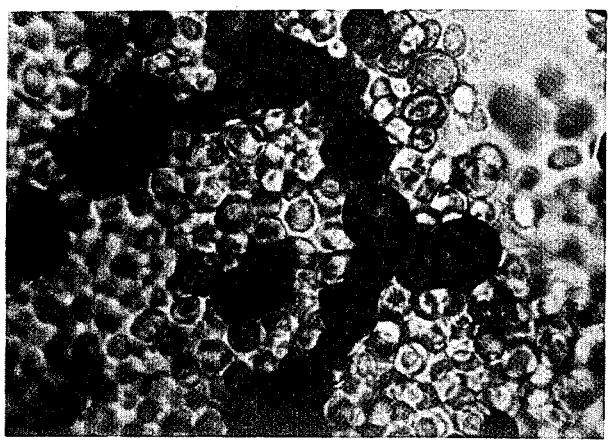
FIG. 16 ×600
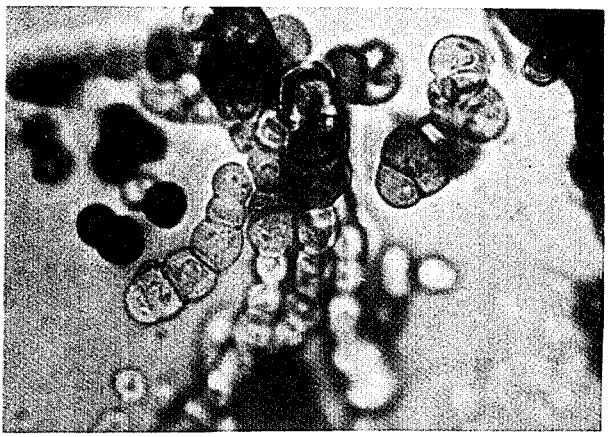
FIG. 17 ×600
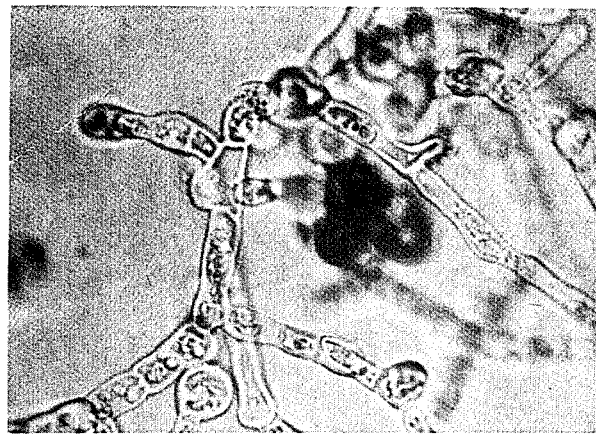
FIG. 18 ×600

×600

×600

×600

×600

PROCESS FOR PRODUCING AN AGGLUTINATING SUBSTANCE UTILIZING DEMATIUM ATCC 20524

BACKGROUND OF THE INVENTION

The present invention relates to a process for producing an agglutinating agent by using a microorganism, more particularly, a process for producing an agglutinating substance having an agglutination activity for not only proteins but also organic substances, inorganic substances, minerals and living germs by culturing a microorganism belonging to Dematium (Dematiaceae) which produce an agglutinating substance.

Further, the present invention relates to a process for agglutinating and sedimenting not only proteins but also organic substances, inorganic substances, minerals and living germs by using an agglutinating substance obtained by culturing a microorganism belonging to Dematium (Dematiaceae) which produces an agglutinating substance.

DESCRIPTION OF THE PRIOR ART

Processes for producing substances having an agglutination-activity for proteins by using microorganisms have already been proposed in, for example, Japanese Patent Laid-Opens Nos. 86189/1976 and 115993/1976. The present invention provides a process for producing an agglutinating substance having an excellent agglutinating activity for not only proteins but also organic substances, inorganic substances, minerals and living germs suspended, dispersed or floating in a liquid by using a microorganism different from those disclosed in said publications and a process for utilizing the same.

BRIEF DESCRIPTION OF DRAWINGS

FIGS. 1 through 9 are graphs showing the results of tests on culture yields, agglutinating properties, etc. of the agglutinating substance produced according to the process of the present invention.

FIGS. 10–18 are microphotographs of the microorganism used in the process of the present invention which comprise photographs of spores, hyphae, diaphragm and mucilages adhering to the spores and hyphae.

SUMMARY OF THE INVENTION

Figure 2:
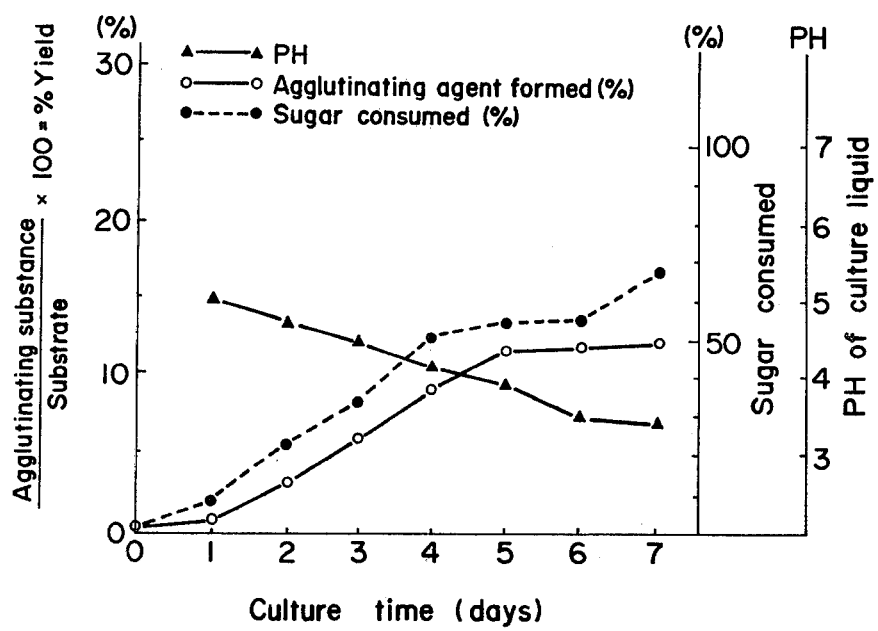

The microorganism used in the process of the present invention is an agglutinating substance-forming microorganism belonging to Dematium (Dematiaceae) including a microorganism of "Biseibutsu Kogyo Gijutsu Kenyu-sho" Deposit No. 4257 i.e. FERM-P No. 4257, and American Type Culture Collection deposit No. 20524 i.e. ATCC No. 20524 (hereinafter referred to as "the microorganism used").

Mycological properties of the microorganism are as follows:

Mycological properties of the isolated germs

The colonies have initially the smooth surface, which grow into yeast-like products in the form of grayish white, mucilaginous, glossy oil drops (fatty). From the periphery of each colony, filiform germs shoot out radiately in all directions which are in the form of curly filaments arranged to form an arborescence. The filiform germs grow well not only on the surface of a culture medium but also in the medium. After a while, light dark brown spots appear on the colony surface, which grow gradually into black spots and finally, the whole surface becomes dark black. From the germs, numerous light brown, elliptic or egg-shaped conidia are formed. The conidia may be separated from one another easily. On the other hand, conidia dot also the surface of the oil drop-shaped colonies.

The culture liquid containing a sugar becomes highly viscous. On the liquid surface, thick, black, moss-like germ masses are formed in the form of colonies. Optimum growth temperature is 20°–25° C. They form alcohols and organic acids from sugars such as glucose and sucrose. They have a specific sweet smell.

1. Culture characteristics* (Note):

a. Solid medium: On potato-glucose-agar medium, the colonies are initially yeast-like colonies in the form of transparent, glossy, viscous, grayish white oil drops. From the periphery of each colony, curly filaments shoot out radially in all directions to form an arborescence. The filiform microbes grow well not only on the surface of the culture medium but also in the medium. Several portions in the arborescence become dark brown. After 3–4 days' culture, faint dark brown spots appear on the colony surface. Thereafter, the spots become faint dark black and increase in number and finally, the spots spread all over the surface to make the whole surface black (7 days' culture). The above characteristics are observed also on Czapek's agar medium but the growth is very slow and about three weeks are required for the blacking of the whole colony surface.

Note)* References: George SMITH, et al. "An Introduction to Industrial Mycology" (pp. 68–97), and "Oyo Biseibutsugaku Kakuron (Special Applied Microbiology)" (pp. 83–87).

b. Liquid medium: In potato-glucose medium, the floating germs grow to form spots (3 days' culture). The colonies increase gradually in number and then the liquid is filled with viscous colonies (7 days' culture). Dark moss-like germ masses appear on the wall of the vessel and gradually, they appear also on the liquid surface (15 days' culture). The microbial rid thus formed are gelatinous, viscous and thick.

In Czapek's medium, they grow similarly but the growth is very slow, germs are small in number and considerable black, moss-like germ masses are formed on the liquid surface after about 3 weeks' culture.

2. Morphological characteristics:

Young cells are transparent, filiform, curly and arborescent. From sides of the microbial body (filiform), black egg-shaped spore-like substances are formed. In the colonies in the form of oil drops, black spore-like spots are formed, which are separated from one another by an impact.

3. Physiological characteristics:

Optimum growth temperature is 20°-25° C. They form mucous products from glucose and sucrose. They form also alcohols and organic acids from sugars such as glucose and have a specific sweet smell.

Separation of germs and detection of agglutinating property:

5% Solution of crude sugar was prepared as separating medium and sterilized by a usual method. 20 Milliliters of the solution were poured in 100 ml. Erlenmeyer flasks, adjusted to a weakly acidic pH and sterilized again. A stock solution (1 ml.) as described below was added to the liquid media and cultured by allowing them to stand at room temperature (25°-30° C.). Sampling was effected every day to measure the agglutination. 1% Solution of kaolin (special grade chemical, a product of Takeda Yakuhin Co.) used for ordinary agglutination tests was prepared and adjusted to a faintly acidic pH to obtain test solution.

The above stock solution was obtained from a dilute solution of crude sugar [i.e. solution dialyzed through a 24 Å (diameter) cellulose membrane] which had been allowed to stand in a beaker during separation and analysis of high molecular polysaccharides contained in glanulated sugar or crude sugar for a long period of time and which had been filtered for a second analysis, since it was found that viscosity of the solution had been increased. In this operation, it was found that the solution exhibited a very remarkable agglutination when a small amount of diatomaceous earth or active carbon was added thereto. Namely, the diatomaceous earth or active carbon was solidified immediately at the bottom of the beaker, suggesting that the solution had a high agglutinating power which cannot be obtained in other commercially available agglutinating agents. Further, it has been confiemed qualitatively that if various substances such as substances containing aluminum silicate as main constituent, for example, kaolin and bentonite; inorganic substances, for example, neutral salts such as calcium carbonate, barium sulfate and silver chloride and organic substances are added to the solution, remarkable agglutination is caused. In this agglutination test, 25 ml. of the test solution were placed in a 50 ml. test tube, then added with 1 ml. of the culture solution and agitated up and down 10 times. After allowing it to stand for three minutes, turbidity of the supernatant liquid was measured with a photoelectric colorimeter at $$\frac{720 \text{ mph}}{10 \text{ mm/cell}}$$

Amount of kaolin remaining in the supernatant liquid was measured by gravimetric method to determine the agglutination. The results were as shown in FIGS. 1 through 9. The agglutination was remarkable in the culture solutions in the initial stage of the culture. This fact indicates that the agglutination-active substance metabolized in the medium exhibits the agglutinating effect even if it is in a small amount. Acetone or butanol odor was strengthened with the passage of time (96 hours). The culture was repeated 10 times, each culture time being 72 hours. A culture liquid having a strong agglutinating power and specific smell (smell of a rose flower) but free of acetone or butanol odor was selected. From the culture liquid, the pure microbacterium was separated out.

Separation of pure microorganism:

A 5% solution of raw sugar or sucrose was prepared, adjusted to pH 5-6, added with 0.2% of powdered yeast extract (a product of Takeda Yakuhin Co.) and then with agar (0.16%), sterilized by heating and poured into laboratory dishes to obtain separation culture media. The culture liquid diluted into concentrations of 1/100, 1/200 and 1/500 with sterilized water was poured in the laboratory dishes (each in a quantity of 1 ml.). After the culture at 30° C., three kinds of colonies were detected. In the initial stage of the culture (about 49 hours' culture), all of the colonies were creamy yellow. In a first case, the center of the colony surface became black with the passage of time and then black hyphae grew on the back surface of the colony centering around the colonies. This fungus will be referred to as "isolated fungus I". In a second case, the cream-yellow colonies were not changed in color but swollen with the passage of time. This microorganism will be referred to as "isolated fungus II". In a third case, the creamy yellow was changed into brown. This microorganism will be referred to as "isolated fungus III".

The above three kinds of fungi thus isolated were cultured by allowing them to stand in the culture liquid of the above described composition. Agglutinating powers of the culture liquids were measured by using 1% kaolin solution. The results were that the agglutination was observed only in isolated microorganism I (wherein the colony surface became black with the passage of time and then black hyphae grew on the back surface of the colony). Apparent viscosity of the culture liquid was increased with the passage of time and the smell specific to this fungus (smell of rose flower) was detected. In other isolated fungi II and III, the agglutination was not detected. In isolated fungi II and III, acetone smell and butyric acid smell were detected, respectively.

Isolated fungus I described above is the agglutinating-substance-forming fungus belonging to Dematium (Dematiaceae) according to the present invention.

Explanation of microphotographs:

Pure-isolated microorganism I was subjected to slant culture in a medium of the following composition and then to liquid culture by allowing it to stand in the same medium.

Composition of medium:

| | |
|---|---|
| Czapek's | Glucose 5% |
| | Sucrose 5% |
| Potato extract | Glucose 5% |
| | Sucrose 5% |
| Yeast extract | Glucose 5% |
| | Sucrose 5% |
| Koji Wasser | Glucose 5% |
| | Sucrose 5% |

When isolated fungus I was cultured according to slant culture in the medium of the above composition, the surface became black. In the photographs of the slantcultured fungus which was then liquid-cultured by allowing it to stand in the medium of the same composition, the culture liquids exhibited greatly increased viscosities. In each medium, a smell specific to this fungus was detected. In a colony obtained by culturing a spore cultured in said medium, the colony surface was black. Microphotographs described below are of fungus separated from this colony.

Microphotographs in FIGS. 10-18 are those of isolated fungus I ($\times 60$, $\times 150$ and $\times 600$) wherein hyphae, grown up spores, diaphragms and mucous substances on the hypha and spore surfaces are recognized.

Figure 3:
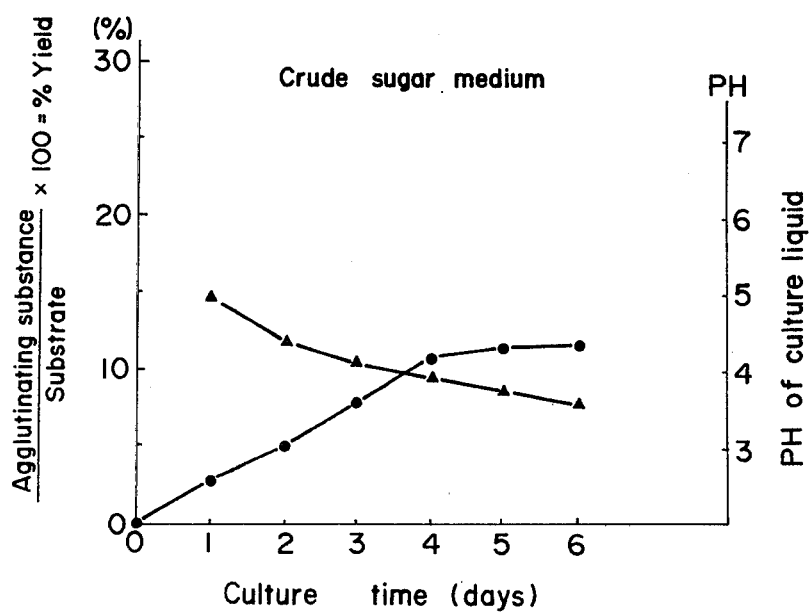
Figure 24:
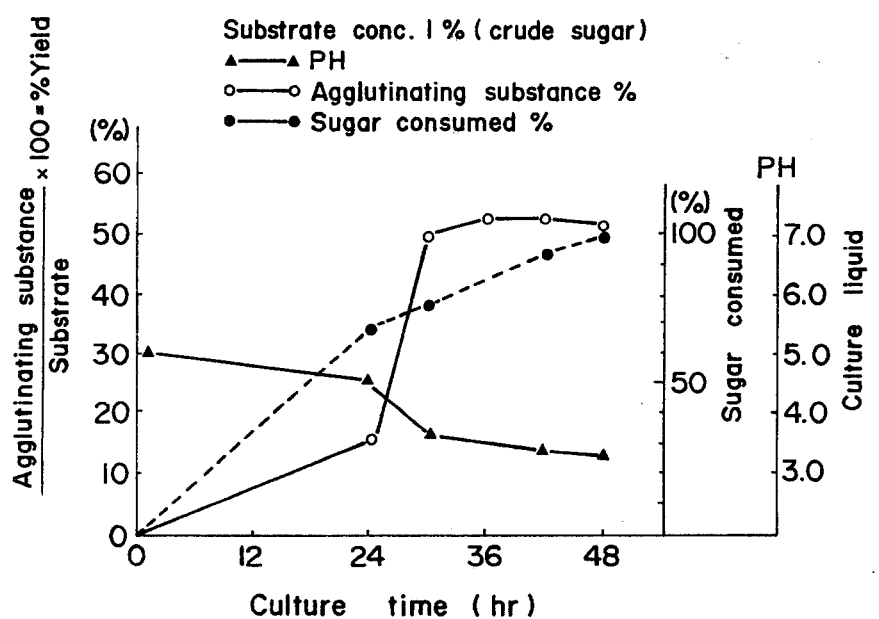
FIG. 24 is a graph showing interrelationships between pH and culture time, between yield (%) of agglutinating substance and culture time and between sugar (substrate) consumption (%) and culture time in the culture of the microorganism of the present invention at a substrate concentration (crude sugar) of 1%.
Figure 25:
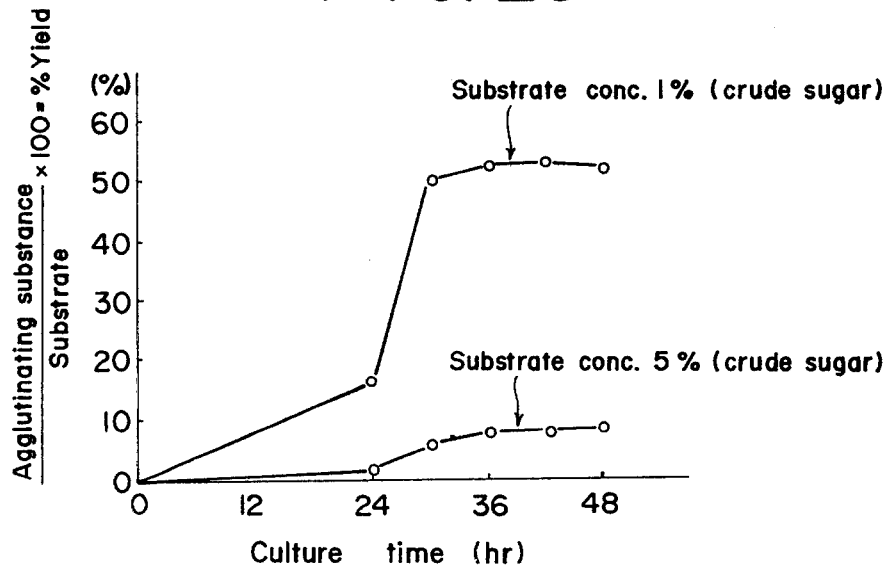
FIG. 25 is a graph showing interrelationships between yield of agglutinating substance and culture time at substrate (crude sugar) concentrations of 1% and 5%.

Culture of fungus I isolated by the inventor and production of agglutinating substance:

Agglutinating substance was produced by using fungus I (Dematium, Dematiaceae) isolated in the pure form as described above under culture conditions as described below. A hexose such as glucose, fructose or galactose, a disaccharide such as sucrose or polysaccharide such as starch was used as carbon source. The carbon source was added with 0.2% of yeast extract. Culture was effected by allowing the same to stand. After one week culture, agglutination of the culture liquid was examined. In all cases, the culture liquid exhibited the agglutination. Amount of the product as compared with the substrate, pH change and remaining sugar were as shown in FIG. 2. Further, in an ordinary synthetic medium such as Czapek's medium in which glucose was incorporated as a carbon source, the culture liquid produced the agglutinating substance in a simple medium containing a carbohydrate as main constituent. For example, if crude sugar is used as the carbon source, the addition of other nutrients (such as N-nutrients and inorganic substances) is unnecessary. Results of agglutinating substance formation when the culture was effected by using a medium comprising only crude sugar are shown in FIG. 3. It was found that in the culture using media of carbon source concentrations ranging from 1% to 20%, amount of the agglutinating substance as compared with the substrate is reduced as the concentration is increased and that a concentration of 1-5%, particularly around 5%, is preferred. Thus, it was judged that since viscosity of the agglutinating substance is very high, the growth of the fungus is physically inhibited when the substance reaches a certain concentration. The fungus was cultured by allowing it to stand in 5-liter fermentation tanks containing a hexose such as glucose, fructose or galactose, a disaccharide such as sucrose or a polysaccharide such as starch as carbon source added with 1% of yeast extract (the total volume of the medium being 3 liters) amount of air being the same in volume (1./min.) as that of the medium; initial pH being 5.0. One week after, agglutination of the culture liquids was examined to reveal that the culture liquids exhibited the agglutination in all cases. Amount of production as compared with the substrate, pH change and remaining sugar were as shown in FIGS. 24 and 25.

Figure 4:
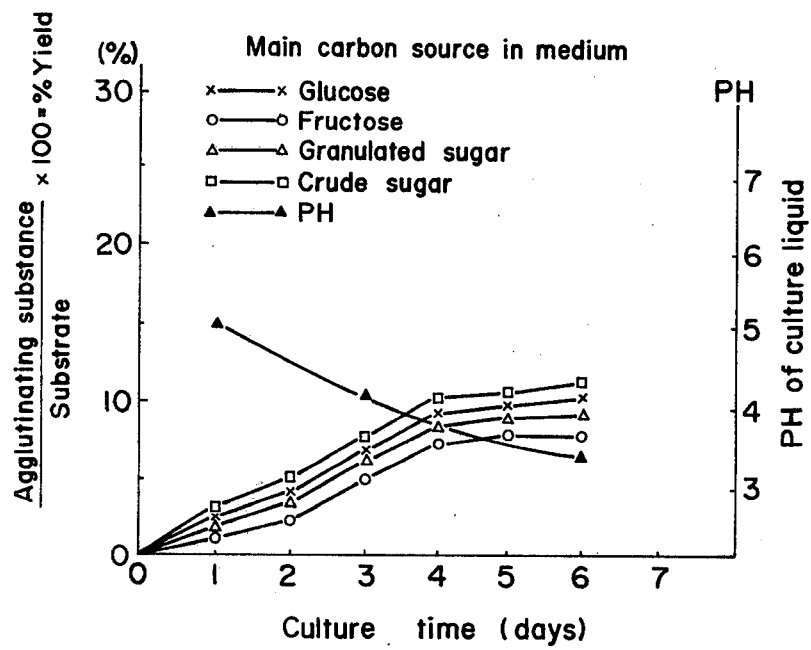

The fact that the intended substances can be obtained in a maximum yield in the medium of a very low carbon source concentration of around 1% indicates that wastes from agricultural industries, stock raising industries and food processing industries having a carbon source (glucose, sucrose, etc.) content as low as about 1% are suitable as the medium for the fungus of the present invention. Accordingly, the present invention also provides an effective process for the treatment of those wastes. If the fungus of the present invention is cultured in the presence of a carbon source-producing fungus, the intended agglutination-active substance can be obtained in a high yield. Thus, the present invention has a great industrial and economical value.

pH is controlled to a faint acidic value in the initial stage of the culture and no precise control is required thereafter. During the culture, the pH value is lowered a little to a stronger acidic value. Though the agglutinating substance is formed in both allowing-to-stand culture and shaking culture, it has been found that the velocity of formation of the agglutinating substance is higher in the shaking culture. Yield of the agglutinating substance is more than 10% based on the substrate (carbon source). The yield is inversely proportional to concentration of the substrate. For example, results of culture are shown in FIG. 4 wherein one of glucose, sucrose, fructose and crude sugar was used as carbon source, 50 ml. of the medium were placed in a 200 ml. Erlenmeyer flask and the culture was effected by allowing it to stand.

Culture conditions and composition of medium:

| Carbon source: | Concentration |
|---|---|
| Glucose | 5% |
| Fructose | 5% |
| Granulated sugar | 5% |
| Crude sugar | 5% |

N source:
  0.2% of yeast powder was added to the medium (excluding crude sugar)
pH:
  Adjusted to 5.0 with HCl.
Temperature:
  28°–30° C.

One milliliter of a culture liquid obtained by shaking culture of said isolated fungus I for 7 days was used as the germs to be inoculated.

Process ① for separation and purification of agglutinating substance produced by isolated fungus I:

A culture liquid obtained by culturing isolated fungus I (Dematium, Dematiaceae) in the above described medium under said culture conditions was heated (100° C./5 mins.) and then subjected to centrifugal precipitation treatment at 3,000 rpm/min. to separate the germs. The germs were removed by filtration. The resulting filtrate was added with ethanol to obtain an ethanol concentration of 30–40% (acetone or methanol may be used in place of ethanol), whereby a membrane is formed between ethanol and the culture liquid. When they were stirred, a fibrous or fluffy substance agglutinated as a mass immediately. Thus agglutinated substance was separated out by centrifugal separation or by twining it round a stirring rod. Then, the agglutinating substance was dissolved again in water, added with ethanol and agglutinated again. After separation followed by drying under reduced pressure, the agglutinating substance was obtained. Thus separated agglutinating substance was grayish white and could be easily pulverized. Photographs in FIGS. 19–22 are electron scanning micrographs of the agglutinating substance. It is inferred that the substance is a homogeneous high molecular weight substance from the fact that it agglutinates immediately in the presence of a low concentration of ethyl alcohol.

Figure 5:
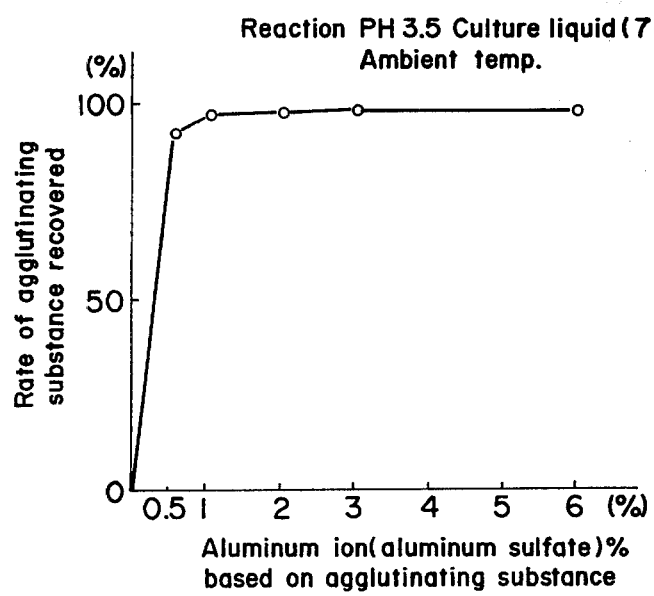
Figure 5:
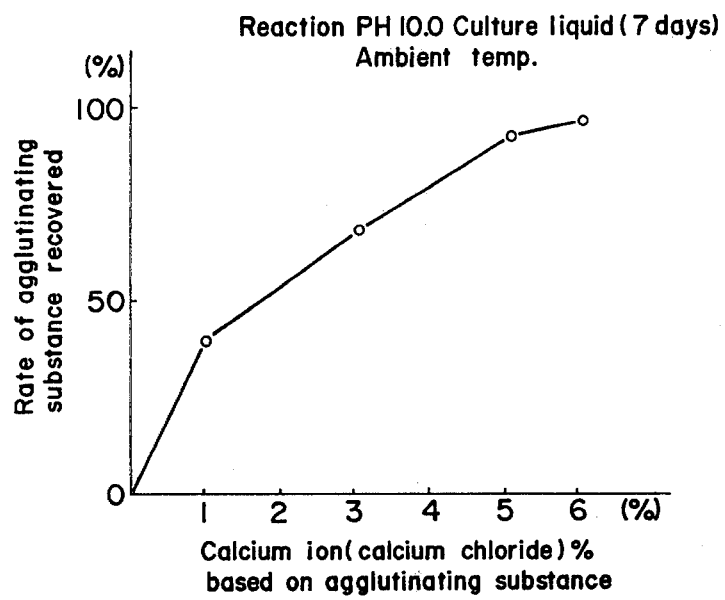

Process ② for purification:

It has been found that the agglutinating substance in the culture liquid agglutinates clearly if aluminum ion is added thereto and that it agglutinates in the presence of calcium ion under alkaline conditions. As aluminum ion to be added, there may be mentioned aluminum sulfate and polymers thereof. As calcium ion, there may be mentioned calcium chloride, lime, etc. Results of agglutination of the substance in the presence of special inorganic ions are as shown in FIG. 5. In due consideration of those properties, a process for separating the agglutinating substance from the culture liquid was established. The process comprises heat-treating the culture liquid (100° C./5 mins.), removing the germs by filtration or centrifugation treatment, adding 0.05–0.10% of an inorganic ion (i.e. an aluminum compound under acidic condition or a calcium compound under alkaline condition), stirring the whole to agglutinate the agglutinating substance completely, separating the same by filtration or centrifugation treatment and drying the product to obtain the agglutinating substance in the form of solid powders.

Process (III) for separation and purification:

The culture liquid is heat-treated (100° C./5 mins.). The germs are removed. The germ-free liquid is concentrated to about 10% to obtain the agglutinating agent. If the agglutinating agent is to be used on a commercial scale, it is very rational to treat the substance in liquid form during the production and use, since the substance is very stable and the liquid product does not need the dissolution before use. The processes for separation and purification of the agglutinating substance will be summarized in the following table.

TABLE

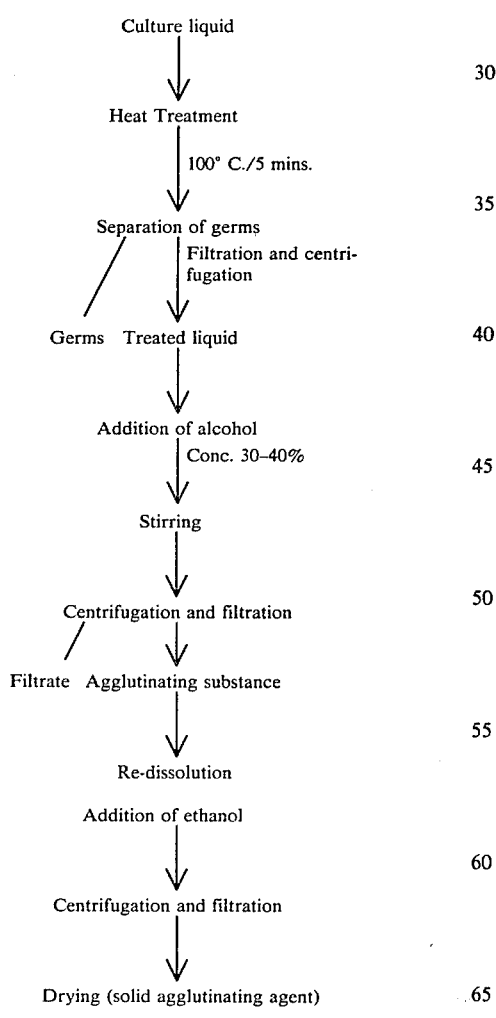

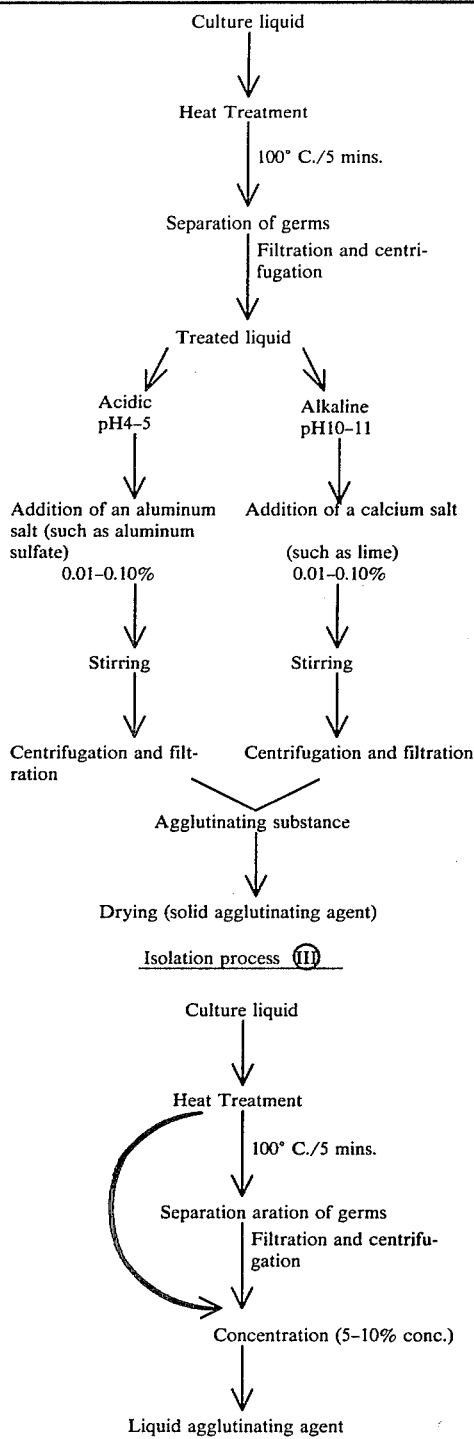

Isolation of the agglutinating substance by addition of inorganic salts:

In isolation process II, concentration of the agglutinating agent in the culture liquid is determined and a culculated amount of an inorganic salt is added thereto in order that the substance reacts with the inorganic salt quantitatively. Residual liquid in isolation process II containing some amount of remaining carbon source is adjusted to a pH value suitable for the culture and used repeatedly. The inorganic ion added such as aluminum ion does not act as inhibitor for the culture of the fungus.

Use or utilization as agglutinating agent:

It has been found that liquid or solid agglutinating substance containing an inorganic ion obtained by culturing the fungus of Dematium (Dematiaceae) and isolated by the process according to the present invention has a property of completely agglutinating and precipitating organic substances, inorganic substances and living germs in the form of dispersion, suspension or colloid in water or floating in water if said substance is added in even a very small amount (0.1-3.0 ppm. based on the liquid). It may safely be said that the agglutinating effect of the agglutinating substance is far stronger than those of commercially available agglutinating agents (inorganic and organic). Another merit of the agglutinating substance is that it does not pose a problem of secondary environmental pollution, since it is a metabolic product of a microorganism.

Figure 6:
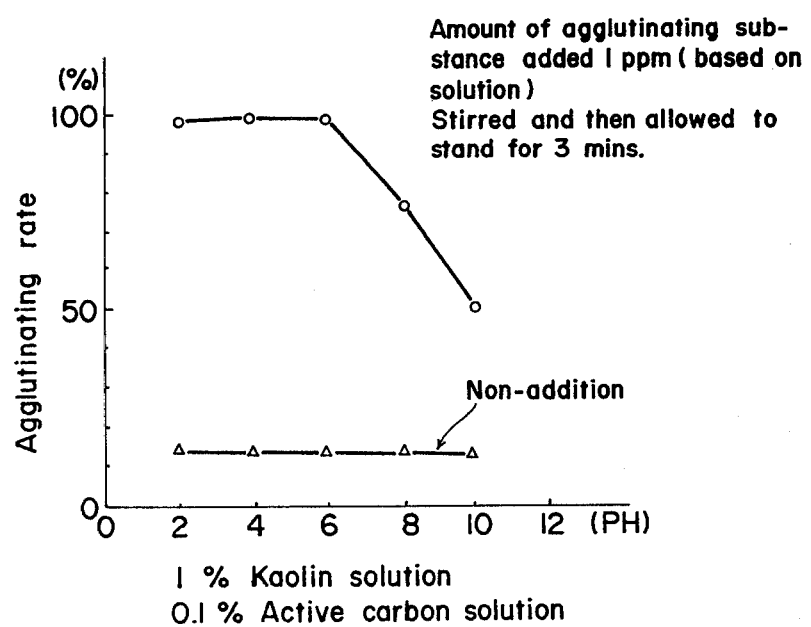
Figure 19:
FIGS. 19 through 22 are electron scanning micrographs of isolated and purified agglutinating substance ($\times 100$, 700 and 1,000).
Figure 20:
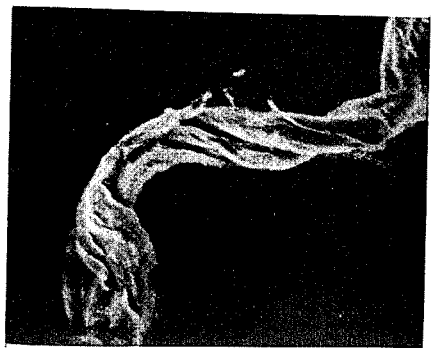
Figure 21:
Figure 22:

Agglutination conditions are as follows:

① Optimum pH range is from acidic to faintly acidic range. Under alkaline condition, the agglutinating power is not exhibited. Results of measurement of agglutinating power of the agglutinating substance under various pH conditions are shown in FIG. 6.

② Reaction temperature ranges from ambient temperature to an elevated temperature. The temperature has no influence on the agglutinating power.

③ Slow stirring is required after the addition of the agglutinating substance.

④ Amount of the substance used as agglutinating agent is 0.1-3.0 ppm. The amount is fixed irrespective of substances to be agglutinated with few marked exceptions. For example, agglutinating properties of the agglutinating substance in an experiment wherein 1% aqueous kaolin solution was used are shown in FIG. 7. It has been found that in case a substance which cannot be agglutinated with this agglutinating substance in acidic pH region such as an aqueous solution of cellulose powder or starch particles is to be agglutinated, the cellulose powder or starch particles can be agglutinated and precipitated immediately by agglutinating the substance, stirring the whole, adding aluminum ion in an amount of 1/30-1/40 of the amount of the agglutinating substance and stirring the whole. Thus, all organic and inorganic substances contained in water in the form of a suspension, dispersion or colloid or floating in water can be agglutinated and precipitated.

Results of agglutination tests of this agglutinating agent in the presence of aluminum ion are shown in FIG. 8. It has been found that though agglutinating power of the agglutinating substance under alkaline condition is very weak, the agglutinating power can be increased to an extent equivalent to that exhibited under alkaline condition by adding calcium ion thereto. Results of tests wherein calcium ion was added under alkaline condition are shown in FIG. 9. Amount of calcium ion added is larger than that of aluminum ion added under acidic condition, i.e. 20-30 parts per part of the agglutinating agent or 40-80 ppm. The experimental results indicate that this agglutinating agent (even in a very small amount) is possible to agglutinate and precipitate organic and inorganic substances contained in water in the form of a suspension, dispersion or colloid or floating in water. The mechanism of the agglutinating effect of said substance is considered to be as follows. The substance having a very high affinity with water (this fact is inferred from the immediate agglutination at a low alcohol concentration) is hydrated in water in such a state that as if a net of very small meshes is charged uniformly in water. If electrically charged finely divided particles of inorganic substance are added thereto, the net loses the electric balance and it is agglutinated, whereby said substance is captured as if fishes are captured with a fishing net. This fact will be clearly understood by observing the agglutination caused by adding a very small amount of aluminum ion to an aqueous solution of this agglutinating agent. If ethanol is added to a solution of the agglutinating substance, it can be observed that membranes are formed in layers between the solution layer and the ethanol layer. The agglutinating substance is used in the form of an aqueous solution. The agglutinating substance containing aluminum or calcium obtained by above process II is used in the form of an alkaline or acidic aqueous solution.

Physicochemical properties of the agglutinating substance:

The agglutinating substance isolated and purified with ethanol is soluble in water. 0.1% Aqueous solution thereof has a specific viscosity of 4-5 which corresponds to that of 40% sugar solution.

Figure 23:
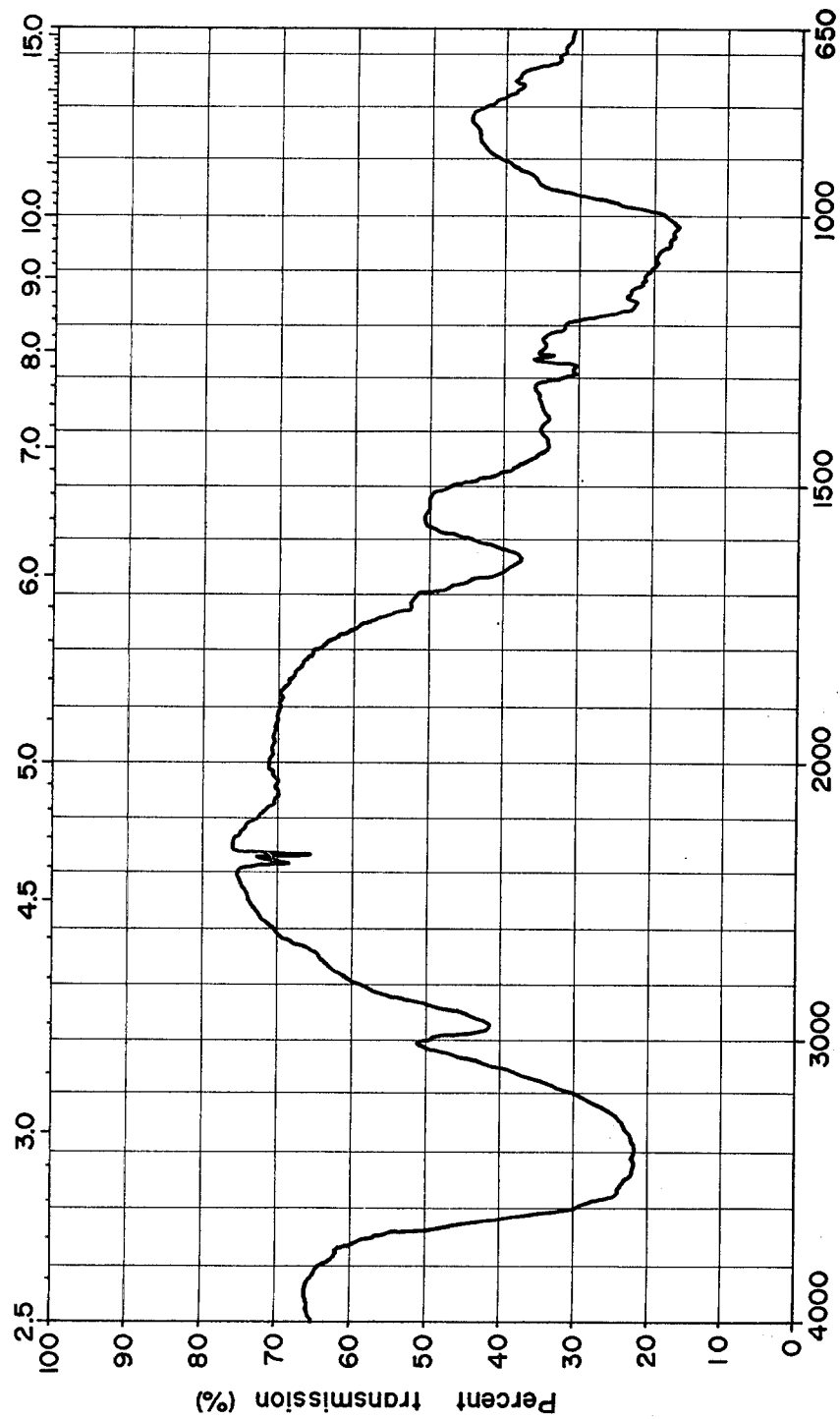
FIG. 23 shows infrared absorption spectrum of the isolated agglutinating substance (KBr method).

Anthrone reaction, Molisch reaction and Biuret reaction of the agglutinating substance is positive. —COOH Qualitative reaction of the substance according to carbazole reaction was also positive. Qualitative determination indicated that its content shown in terms of galacturonic acid was 10-15%. When the substance was hydrolyzed with 1 N $H_2SO_4$ for 24 hours, non-decomposed substance remained and sugar composition of the hydrolyzate comprised glucose, galactose and mannose according to paper chromatography. Results of infrared chromatography of the agglutinating substance are shown in FIG. 23, wherein absorption due to —COOH was recognized but absorption due to amido group, etc. was unclear.

The agglutinating substance is considered to be a high molecular weight substance mainly comprising glucose and galactose and containing organic acids.

Viscosity of the agglutinating substance isolated and purified from culture liquid:

| Sample conc. | | Relative viscosity (CP) |
|---|---|---|
| g/100 ml | yel | (30° C., pH 6.5) |
| 0.01 | 1,620 | |
| 0.05 | 2,200 | No change in viscosity |
| 0.10 | 5,200 | under acidic and |
| | | alkaline conditions |
| | 1,000 | |
| g/100 ml | yel | |
| | 30° C. | 55° C. |
| 0.01 | 1,620 | 1,610 |
| 0.05 | 2,200 | 2,100 |
| 0.10 | 5,200 | 5,100 |

Elementary analysis of the isolated, purified agglutinating substance:

| | |
|---|---|
| H | 6.52% |
| C | 41.04 |
| N | 0.14 |
| O | 51.74 |
| Ash | 0.56 (hygroscopic) |

Molecular weight:
More than 1,000,000 (presumed)

Qualitative reactions:

| | |
|---|---|
| Anthrone reaction | + |
| Carbazole reaction | + |
| Biuret reaction | + |
| Ninhydrin reaction | + |

Solubility of the isolated, purified agglutinating substance:

| Solvent | Solubility |
|---|---|
| Water | Soluble in cold and warm water (but difficulty soluble at a conc. of more than 10%) |
| Ethanol | Insoluble |
| Methanol | " |
| Acetone | " |
| Carbon tetrachloride | " |
| Butanol | " |
| Ether | " |

Solubility in ethanol:

| Ethanol concentration % | Solubility |
|---|---|
| Less than 40% | Soluble |
| 40–45% | Insoluble (albumen-like liquid is formed; high water retention characteristics) |
| More than 45% | Albumen-like liquid or membrane (collodion membrane)-like substance is formed, which agglutinates to form fluffy solid |

Properties of the isolated, purified agglutinating substance:

| | |
|---|---|
| Smell: | None |
| Taste: | None |
| Hygroscopicity: | Weak (ambient temperature) |
| Color: | Grayish brown fibrous substance |

If a divalent or trivalent ion or heavy metal ion such as $Ca^{++}$, $Al^{---}$, Mg, Zn or Pd (equivalent or less than 1/10 amount) is added to a dilute solution (concentration: 1–100 ppm) of the agglutinating substance, the substance agglutinates completely to form fibrous substance. Reaction of the agglutinating substance with an inorganic ion proceeds quantitatively.

DETAILED DESCRIPTION OF THE PREFERRED EMBODIMENTS:

EXAMPLE 1

Test results of raw water in Water Purification Plant of Miyazaki city:

TABLE 1

| | Amount of agglutinating agent added (ppm) | | | | | |
|---|---|---|---|---|---|---|
| | 0 | 1 | 2 | 3 | 4 | |
| 7.6* | 95.0% | 99.5% | 99.5% | 99.6% | 99.7% | |
| 6.0 | 95.0 | 99.5 | 99.8 | 99.9 | 99.9 | Percent |
| 5.0 | 95.0 | 99.5 | 99.8 | 99.9 | 99.9 | trans- |
| 4.0 | 95.0 | 99.0 | 99.4 | 99.5 | 99.5 | mission |

(Note)
*7.6: pH of raw water

Raw water was added with agglutinating agent (agglutinating agent produced by microorganism), stirred for 5 minutes (60 rpm/min.) and allowed to stand for 5 minutes. Percent transmission of thus resulting supernatant liquid was measured (wave length: 720 mμ) by using distilled water as control to obtain the results as shown in Table 1.

It was found that as clearly shown by Table 1, inorganic and organic substances contained in the raw water in the form of suspension or colloid are converted immediately into flocks of a high precipitating property by adding several ppm (i.e. 1–4 based on the raw water) of the agglutinating agent thereto, whereby percent transmission of the water is increased to 99.9% which is equivalent to that of distilled water. It is understood from this fact that the agglutinating agent produced by the microorganism by the inventor can be used advantageously as agglutinating agent for removing substances contained in the form of a colloid or suspension in a raw water in water purification plants, etc. Usually, in a water purification treatment (for industrial water or city water), 20–30 ppm (at most 100 ppm) of aluminum sulfate is added thereto for reducing turbidity of the water to less than 1 ppm and flocks thus formed are precipitated and removed in a precipitation tank. However, if the agglutinating agent produced by the microorganism according to the present invention is used, amount thereof is only 1–2 ppm and the flocks formed can be precipitated very well. Thus, it is considered that the apparatus for the water treatment can be rationalized.

If several ppm of the agglutinating agent produced from the microorganism are added to a raw water to be purified and then 1–2 ppm of aluminum sulfate are added thereto, percent transmission of the water is increased to a value higher than that attained by using only the agglutinating agent. Namely, percent transmission of water thus treated is comparable to that of distilled water. The results are shown in Table 2.

TABLE 2

| pH of raw water | Agglutinating agent + aluminum sulfate 1 ppm + 1 ppm | Not added | |
|---|---|---|---|
| 7.6 | 100% | 95.0% | Percent |
| 6.0 | 100 | 95.0 | trans- |
| 5.0 | 100 | 95.0 | mission |
| 4.0 | 99.9% | 95.0 | |

EXAMPLE 2

Test results of treatment of waste water from sugar industry (waste water containing fine particles of active carbon):

TABLE 3-1

| pH of raw water | Agglutinating agent (2 ppm) | Agglutinating agent (2 ppm) Aluminum sulfate (1 ppm) | |
|---|---|---|---|
| 9 | 84% | 86.0% | |
| 8 | 87 | 98.0 | |
| 7 | 89 | 99.0 | Percent |
| 6 | 90 | 99.5 | transmission |
| 5 | 88 | 99.0 | |
| 4 | 84 | 98.0 | |
| 3 | 84 | 98.0 | |

TABLE 3-2

| Amount of agglutinating agent added (ppm) | Aluminum sulfate (1 ppm) | |
|---|---|---|
| 0.5 | 98.5% | Percent |
| 1.0 | 99.0 | trans- |
| 1.5 | 99.0 | mission |
| 2.0 | 99.5 | |
| 3.0 | 99.5 | |

Analysis of untreated water containing fine particles of active carbon:

| pH: | 10.5 |
|---|---|
| SS | 40-50 |
| Average particle diameter: | less than 320 megh |
| Percent transmission T %: | 83 |
| Apparent color: | Black |

Fine carbon particles contained in a waste water from a sugar manufactory (wash solution from carbon particle regeneration step) are hardly sedimented usually even if the water is allowed to stand for a long period of time (24-48 his) and the water is not changed in color (black). However, it was found that by adding 1-3 ppm of the agglutinating agent produced by the microorganism according to the present invention to the water, then adjusting the water to around pH 7 and adding 1 ppm of aluminum sulfate thereto, the carbon flocks are formed immediately and the flocks are precipitated to make the water transparent like distilled water. The test results are shown in Table 3.

Insoluble suspensoids such as fine particles of active carbon can be agglutinated completely by the agglutinating agent of the present invention by using the agglutinating agent together with aluminum sulfate at around pH 7. The agglutinating effect can be obtained even if concentration of the suspensoid is very low (such as several ppm).

EXAMPLE 3

Test results of treatment of a pulp waste water (Kp waste water from K. Co.):

A pulp waste water (Kp waste water) was diluted to a concentration of 1/10 and adjusted to pH 6.0 to obtain a sample for the experiment.

TABLE 4

| Amount of aluminum sulfate added (ppm) | Agglutinating agent (ppm) | Decoloring rate of supernatant liquid | Rate of removal of insoluble matter from liquid |
|---|---|---|---|
| 400 | 20 | 46.0% | 80.0% |
| 600 | 20 | 61.2 | 95.0 |
| 800 | 20 | 70.0 | 98.0 |
| 1000 | 20 | 99.7 | 99.9 |
| 0 | 0 | 0 | 0 |

Decoloring rate:

Decoloring rate was measured at a wave length of 420 mμ by using distilled water as control. Rate of the treated water was compared with that of the raw water. Aluminum sulfate was added after the addition of the agglutinating agent.

A pulp waste water (Kp waste water) is diluted to a concentration of 1/10, added with the agglutinating agent produced by microorganism according to the present invention, stirred and then added with aluminum sulfate to form a large amount of flocks from soluble matters, whereby the supernatant liquid becomes transparent. The flock formation and precipitation of the flocks thus formed are completed in several minutes. When the agglutinating agent is used for the treatment of pulp waste water, the water is adjusted to a neutral pH and diluted to a concentration of about 1/10. In the treatment of the pulp waste water with the agglutinating agent, effects of decoloration and insolubilization of soluble matter are particularly remarkable. The flocks formed can be filtered out very easily.

EXAMPLE 4

Test results of treatment of waste water from a noodle-making device:

TABLE 5

| pH | Percent transmission | C.O.D. Removal rate % |
|---|---|---|
| 3 | 61 | 40.1 |
| 4 | 59 | 50.0 |
| 5 | 59 | 50.0 |
| 6 | 89 | 81.1 |
| 7 | 88 | 80.0 |
| | 30 | 0 |
| | | (5667 ppm) |

Waste water from a noodle-making device

| pH 6.0 | |
|---|---|
| C.O.D. | 5667 ppm |
| S.S | 4100 ppm |

By adding 6-9 ppm of the agglutinating agent produced by the microorganism according to the present invention to a waste water from a noodle-making device in the presence of 2 ppm of aluminum sulfate, C.O.D. could be reduced by 80% and percent transmission could be increased to 89-88%. It was found that the agglutination can be completed in several minutes and the agglutinated substances can be filtered out very easily.

Treatment of waste water from a noodle-making device is usually very difficult and process for the treatment has not been established yet. It has been found that quality of the waste water from noodle-making device can be improved remarkably by adding several ppm of the agglutinating agent of the present invention. In case C.O.D. concentration of S.S. concentration of the waste water is too high, it is preferred to dilute the water to a concentration of about 2,000 ppm before the treatment with the agglutinating agent.

EXAMPLE 5

Test results of treatment of waste water from a bean jam-making device:

TABLE 6

| pH | Amount of CaO added ppm | Agglutinating agent ppm | Decoloring rate % | Removal rate % |
|---|---|---|---|---|
| 10.8 | 500 | 2 | 0 | 72.2 |
| 11.2 | 1,000 | 2 | 43 | 75.7 |
| 12.2 | 5,000 | 2 | 68 | 79.2 |
| 12.3 | 10,000 | 2 | 73 | 86.1 |

Waste water from a bean jam-making device:

| | |
|---|---|
| pH | 6.2 |
| Red C.O.D. | 5750 ppm |
| S.S. | 1680 ppm |

The waste water from bean jam-making device is adjusted to pH 10-12 with CaO and added with 2 ppm of the agglutinating agent of the present invention to reduce C.O.D. of the water by more than 70%. The flocks thus formed can be precipitated very easily. If the waste water of pH 6-8 is treated with the same agent in the presence of aluminum sulfate, decoloration and C.O.D. removal rate are poor.

EXAMPLE 6

Test results of treatment of urine and waste water from a swinery:

TABLE 7

| | | | Supernatant liquid | | |
|---|---|---|---|---|---|
| pH | Agglutinating agent added ppm | Aluminum sulfate added ppm | Percent transmission T % | Decoloring rate % | C.O.D. Removal rate % |
| 4.0 | 20 | 100 | 98-99 | 95 | 35 |
| 5.0 | 20 | 100 | 98-99 | 95 | 35 |
| 6.0 | 20 | 100 | 98-99 | 95 | 40 |
| 7.0 | 20 | 100 | 98-99 | 95 | 40 |

TABLE 8 pH 6.0

| Agglutinating agent added ppm | Aluminum sulfate added ppm | Percent transmission T % | Decoloring rate % | C.O.D. Removal rate % |
|---|---|---|---|---|
| 50 | 100 | 95-98 | 95.0 | 40 |
| 40 | 100 | 96-98 | 95.0 | 40 |
| 20 | 100 | 98-99 | 95.0 | 40 |
| 10 | 100 | 98-99 | 95.0 | 40 |

Urine and waste water from a swinery:

| | |
|---|---|
| C.O.D.: | 436 |
| pH: | 7.2 |
| Brown, cloudy | |
| T %: | 55 |

The urine and waste water from swinery are added with the agglutinating agent of the present invention and then aluminum sulfate. White fluffy flocks are formed immediately. The flocks are precipitated very easily to leave transparent supernatant liquid. Percent transmission thereof is up to 99.0%. Decoloring rate is 95.0% and, simultaneously, C.O.D. can be reduced by 40%. The flocks thus precipitated can be filtered out very easily. Amount of the flocks thus precipitated is 0.1-0.04% based on 100 ml. of the swinery waste water and urine.

Urine and waste water from swinery have been treated generally by various processes. However, many problems such as color, C.O.D. and turbidity of the treated water have not been solved. If the agglutinating agent produced by the microorganism according to the present invention is used for the treatment, percent transmission can be improved and decoloring rate can be reduced remarkably and C.O.D. can also be reduced. Thus, said problems can be solved and the treatment can be rationalized.

EXAMPLE 7

Test results of agglutination treatment of microbial sludges from a liquid obtained by treatment of urine and waste water from swinery with photosynthetic bacteria:

Waste waters from stock farms such as urines from a swinery have heretofore been treated with photosynthetic bacteria disclosed in the specification of Japanese Patent Publication No. 11979/1976. However, the separation of microbial sludges from the treated liquid by sedimentation is very difficult and, therefore, a means of overcoming this defect has been desired. If the agglutinating substance produced by the microorganism according to the present invention is used together with aluminum sulfate, the separation can be effected very rapidly and cmpletely and, in addition, color and percent transmission of the supernatant liquid are improved. The excellent results of the test was obtained on a liquid obtained by treatment with photosynthetic bacteria.

Percent transmission (T) of the supernatant liquid was 99-99.5% and decoloring rate was more than 50%. The water thus treated had the same appearance as colorless transparent water.

The above results indicate that the agglutinating substance exhibits a remarkable effect on liquids and waste waters containing microorganisms, particularly bacteria and that the agglutinating substance can be utilized advantageously for the treatment of waste waters by sedimentation.

What we claim is:

1. A process for producing an agglutinating substance comprising cultivating an agglutinating substance-producing fungus having the identifying characteristics of Dematium ATCC 20524 at an acidic pH in a culture medium containing a carbon source until an agglutinating substance is produced and separating the agglutinating substance from the culture medium.

2. The process for producing an agglutinating substance according to claim 1 wherein a carbohydrate is employed as the main carbon source.

3. The process for producing an agglutinating substance according to claim 2 wherein the carbon source content in the culture medium is 0.5 to 5%.

* * * * *